United States Patent [19]
Greenlee et al.

[11] Patent Number: 5,246,944
[45] Date of Patent: Sep. 21, 1993

[54] QUINOLINE ANGIOTENSIN II ANTAGONISTS INCORPORATING A SUBSTITUTED BENZYL ELEMENT

[75] Inventors: William J. Greenlee, Teaneck; Prasun K. Chakravarty, Edison, both of N.J.

[73] Assignee: Merck & Co., Inc., Rahway, N.J.

[21] Appl. No.: 744,140

[22] Filed: Aug. 13, 1991

[51] Int. Cl.[5] ............... C07D 215/20; C07D 215/233; A61K 31/47
[52] U.S. Cl. .................. 514/312; 514/314; 546/14; 546/153; 546/156
[58] Field of Search ............... 546/153, 156; 514/312, 514/314

[56]  References Cited
U.S. PATENT DOCUMENTS 5,177,095  1/1993  Greenlee et al. ............ 514/384
5,183,810  2/1993  Greenlee et al. ............ 514/63

FOREIGN PATENT DOCUMENTS

0323841A3  1/1988  European Pat. Off. ......... 548/266.2
0487252A1  11/1990  European Pat. Off. ......... 546/122
WO92/02508  7/1991  PCT Int'l Appl. ............ 546/153

OTHER PUBLICATIONS

Chemical Abstracts, vol. 86, No. 21, AB#155541b (1977).

Primary Examiner—Alan L. Rotman
Attorney, Agent, or Firm—Joseph F. DiPrima; Valerie J. Camara

[57] ABSTRACT

Substituted quinolines and azaquinolines (1,5-naphthridines) attached through an oxymethylene bridge to novel substituted phenyl derivatives of the Formula I, are useful as angiotensin II antagonists.

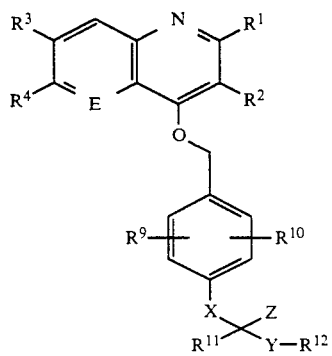

8 Claims, No Drawings

QUINOLINE ANGIOTENSIN II ANTAGONISTS INCORPORATING A SUBSTITUTED BENZYL ELEMENT

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. Clin. Exp. Hypertens. A4, 27-46 (1982); D. H. P. Streeten and G. H. Anderson, Jr.—Handbook of Hypertension, Clinical Pharmacology of Antihypertensive Drugs, ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [Eur. J. Pharm. Exp. Therap, 157, 13-21 (1988)] and by P. C. Wong, et al. [J. Pharm. Exp. Therap, 247, 1-7 (1988)]. European Patent Application 245,637 discloses derivatives of 4,5,6,7-tetrahydro-2H-imidazo[4,5-c]-pyridine-6-carboxylic acid and analogs thereof as antihypertensive agents. Recent publications EP 412,848 and WO 91/07404 describe quinoline and azaquinoline derivatives, respectively, as AII antagonists.

None of the compounds disclosed within this application have been claimed or disclosed in any published patents or articles, including the abovementioned publications.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of Formula I:

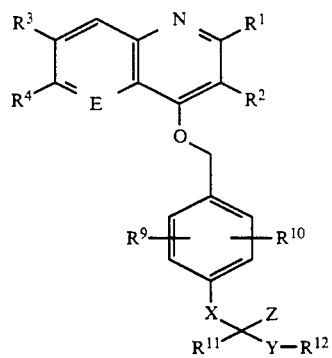

FORMULA I or a pharmaceutically acceptable salt thereof wherein:
$R^1$ is:
  (a) H,
  (b) $(C_1-C_8)$-alkyl,
  (c) $(C_3-C_8)$-cycloalkyl,
  (d) $(C_3-C_8)$-cycloalkyl-$(C_1-C_4)$-alkyl,
  (e) $(C_1-C_8)$-perfluoroalkyl,
  (f) phenyl, or
  (g) phenyl-$(C_1-C_4)$-alkyl; and
$R^2$ is:
  (a) H,
  (b) $(C_1-C_8)$-alkyl,
  (c) $(C_3-C_8)$-cycloalkyl,
  (d) $(C_3-C_8)$-cycloalkyl-$(C_1-C_4)$-alkyl,
  (e) $CO_2R^{5a}$,
  (f) $(C_1-C_4)$-alkoxycarbonyl,
  (g) CN,
  (h) $NO_2$,
  (i) phenyl, or
  (j) phenyl-$(C_1-C_4)$-alkyl; and
$R^3$ and $R^4$ are independently:
  (a) H,
  (b) $(C_1-C_6)$-alkyl, unsubstituted or substituted with a substituent selected from the group consisting of:
    (i) aryl, wherein aryl is defined as phenyl or naphthyl,
    (ii) $(C_3-C_7)$-cycloalkyl,
    (iii) $NR^5R^{21}$,
    (iv) morpholin-4-yl,
    (v) OH,
    (vi) $CO_2R^{5a}$, or
    (vii) $CON(R^5)_2$,
  (c) $(C_1-C_6)$-alkoxy,
  (d) $(C_1-C_4)$-perfluoroalkoxy,
  (e) Cl, Br, F, I,
  (f) $CF_3$,
  (g) CN,
  (h) $NO_2$,
  (i) OH,
  (j) $NH_2$,
  (k) $NH[(C_1-C_6)$-alkyl],
  (l) $N[(C_1-C_6)$-alkyl$]_2$,
  (m) $N(CH_2CH_2)_2O$,
  (n) $N(CH_2CH_2)_2NCOR^{5a}$,
  (o) $N(CH_2CH_2)_2NR^{5a}$,
  (p) $CO_2R^{5a}$,
  (q) $(C_1-C_4)$-alkoxycarbonyl,
  (r) $CONH_2$,
  (s) $CONH[(C_1-C_7)$-alkyl],
  (t) $CON[(C_1-C_7)$-alkyl$]_2$, (u) R³ and R⁴ may optionally together form a ($C_1$-$C_4$)-alkylenedioxy group;

x is 0 to 2;
m is 1 to 5;
p is 0 to 3;
n is 1 to 10;
E is: CH or N;
$R^5$ is:
  (a) H, or
  (b) ($C_1$-$C_6$)-alkyl, and
$R^{5a}$ is:
  (a) $R^5$,
  (b) $CH_2$-aryl, or
  (c) aryl; and
$R^9$ and $R^{10}$ are independently:
  (a) H,
  (b) ($C_1$-$C_6$)-alkyl, unsubstituted or substituted with ($C_3$-$C_7$)-cycloalkyl,
  (c) ($C_2$-$C_6$)-alkenyl,
  (d) ($C_2$-$C_6$)-alkynyl,
  (e) Cl, Br, F, I,
  (f) ($C_1$-$C_6$)-alkoxy,
  (g) when $R^9$ and $R^{10}$ are on adjacent carbons, they can be joined to form a phenyl ring,
  (h) ($C_1$-$C_6$)-perfluoroalkyl,
  (i) ($C_3$-$C_7$)-cycloalkyl, unsubstituted or substituted with ($C_1$-$C_6$)-alkyl,
  (j) aryl,
  (k) ($C_1$-$C_6$)-alkyl-S(O)$_x$-(CH$_2$)$_n$-,
  (l) hydroxy-($C_1$-$C_6$)-alkyl,
  (m) —$CF_3$,
  (n) —$CO_2R^{5a}$,
  (o) —OH,
  (p) —$NR^5R^{21}$,
  (q) —[($C_1$-$C_6$)-alkyl]$NR^5R^{21}$,
  (r) —$NO_2$,
  (s) —(CH$_2$)$_n$-SO$_2$-N($R^5$)$_2$,
  (t) —$NR^5CO$-($C_1$-$C_4$)-alkyl, or
  (u) —CON($R^5$)$_2$; and
X is:
  (a) —O—,
  (b) —S(O)$_x$—,
  (c) —$NR^{13}$—,
  (d) —CH$_2$O—,
  (e) —CH$_2$S(O)$_x$—
  (f) —CH$_2$NR$^{13}$—,
  (g) —OCH$_2$—,
  (h) —NR$^{13}$CH$_2$—,
  (i) —S(O)$_x$CH$_2$—,
  (j) —CH$_2$—,
  (k) —(CH$_2$)$_2$—,
  (l) single bond, or
  (m) —CH=, wherein Y and $R^{12}$ are absent forming a —C=C— bridge to the carbon bearing Z and $R^{11}$; and
Y is:
  (a) single bond,
  (b) —O—,
  (c) —S(O)$_x$—,
  (d) —NR$^{13}$—, or
  (e) —CH$_2$—; and
except that X and Y are not defined in such a way that the carbon atom to which Z is attached also simultaneously is bonded to two heteroatoms (O, N, S, SO, $SO_2$):
$R^{11}$ and $R^{12}$ are independently:
  (a) H,
  (b) ($C_1$-$C_6$)-alkyl, unsubstituted or substituted with a substituent selected from the group consisting of:
    (i) aryl,
    (ii) ($C_3$-$C_7$)-cycloalkyl,
    (iii) $NR^5R^{21}$,
    (iv) morpholin-4-yl,
    (v) OH,
    (vi) $CO_2R^{5a}$, or
    (vii) CON($R^5$)$_2$,
  (c) aryl or aryl-($C_1$-$C_2$)-alkyl, unsubstituted or substituted with 1 to 3 substitutents selected from the group consisting of:
    (i) Cl, Br, I, F,
    (ii) ($C_1$-$C_6$)-alkyl,
    (iii) [($C_1$-$C_5$)-alkenyl]$CH_2$-,
    (iv) [($C_1$-$C_5$)-alkynyl]$CH_2$-,
    (v) ($C_1$-$C_6$)-alkyl-S(O)$_n$-(CH$_2$)$_n$-,
    (vi) —$CF_3$,
    (vii) —$CO_2R^{5a}$,
    (viii) —OH,
    (ix) —$NR^5R^{21}$,
    (x) —$NO_2$,
    (xi) —$NR^5COR^5$,
    (xii) —CON($R^5$)$_2$,
    (xiii) —G-[($C_1$-$C_6$)-alkyl]-$R^{23}$,
    (xiv) —N[CH$_2$CH$_2$]$_2$Q, or
    (xv) —P(O)[O-($C_1$-$C_4$)-alkyl]$_2$,
    (xvi) —$OCH_3$,
and can additionally be substituted with 1 or 2 substituents selected from the group consisting of: Br, Cl or F,
  (d) ($C_3$-$C_7$)-cycloalkyl, or
  (e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, S(O)$_x$ and $NR^{22}$; and
G is: a single bond, O, S(O)$_x$ or $NR^{23}$; and
Q is: O, S(O)$_x$ or $NR^{22}$; and
$R^{13}$ is:
  (a) H,
  (b) ($C_1$-$C_6$)-alkyl,
  (c) aryl,
  (d) aryl-($C_1$-$C_6$)-alkyl-(C=O)-,
  (e) ($C_1$-$C_6$)-alkyl-(C=O)-,
  (f) [($C_2$-$C_5$)-alkenyl]$CH_2$-,
  (g) [($C_2$-$C_5$)-alkynyl]$CH_2$-, or
  (h) aryl-CH$_2$-; and
Z is:
  (a) —$CO_2H$,
  (b) —$CO_2R^{24}$,
  (c) —tetrazol-5-yl,
  (d) —CONH(tetrazol-5-yl)
  (e) —CONHSO$_2$-aryl,
  (f) —CONHSO$_2$-($C_1$-$C_8$)-alkyl, wherein the alkyl group is unsubstituted or substituted with a substituent selected from the group consisting of: —OH, —SH, —O($C_1$-$C_4$)-alkyl, —S—($C_1$-$C_4$)-alkyl, —$CF_3$, Cl, Br, F, I, —$NO_2$, —$CO_2H$, —$CO_2$-($C_1$-$C_4$)-allyl, —$NH_2$, —NH[($C_1$-$C_4$)-alkyl], —N[($C_1$-$C_4$)-alkyl]$_2$; and
  (g) —CONHSO$_2$-($C_1$-$C_4$)-perfluoroalkyl,
  (h) —CONHSO$_2$-heteroaryl, or
  (i) —CONHSO$_2$NR$^{5a}$R$^{5a}$; and
  (j) —SO$_2$NHCO-aryl,
  (k) —SO$_2$NHCO—($C_1$-$C_8$)-alkyl, wherein the alkyl group is unsubstituted or substituted with a substituent selected from the group consisting of:

—OH, —SH, —O($C_1$–$C_4$)-alkyl, —S—($C_1$–$C_4$)-alkyl, —$CF_3$, Cl, Br, F, I, —$NO_2$, —$CO_2H$, —$CO_2$-($C_1$–$C_4$)-alkyl, —$NH_2$, —NH[($C_1$–$C_4$)-alkyl], —N[($C_1$–$C_4$)-alkyl]$_2$; and (l) —$SO_2$NHCO-($C_1$–$C_4$)-perfluoroalkyl,
(m) —$SO_2$NHCO-heteroaryl,
(n) —$SO_2$NHCONR$^{5a}$R$^{5a}$,
(o) —PO(OH)$_2$,
(p) —PO(OR$^5$)$_2$, or
(q) —PO(OH)(OR$^5$); and R$^{20}$ is:
(a) aryl, or
(b) heteroaryl, unsubstituted or substituted with one or two substituents selected from the group consisting of:
  (i) ($C_1$–$C_4$)-alkyl,
  (ii) ($C_1$–$C_4$)-alkoxyl,
  (iii) Br, Cl, I, F, or
  (iv) $CH_2$-aryl; and R$^{21}$ is:
(a) H, or
(b) ($C_1$–$C_4$)-alkyl, is unsubstituted or substituted with:
  i) $NH_2$,
  ii) NH[($C_1$–$C_4$)-alkyl],
  iii) N[($C_1$–$C_4$)-alkyl]$_2$,
  iv) $CO_2H$,
  v) $CO_2$($C_1$–$C_4$)-alkyl,
  vi) OH,
  vii) $SO_3H$, or
  viii) $SO_2NH_2$; and R$^{22}$ is:
(a) H,
(b) ($C_1$–$C_4$)-alkyl,
(c) ($C_1$–$C_4$)-alkoxyl,
(d) aryl,
(e) aryl-($C_1$–$C_4$)-alkyl,
(f) $CO_2$R$^{5a}$,
(g) CON(R$^5$)$_2$,
(h) $SO_2$R$^{5a}$,
(i) $SO_2$N(R$^5$)$_2$,
(j) P(O)[($C_1$–$C_4$)-alkoxyl]$_2$, or
(k) imidazol-2-yl or imidazol-4-yl, in which the imidazolyl can be substituted with ($C_1$–$C_4$)-alkyl; and R$^{23}$ is:
(a) OH,
(b) NR$^5$R$^{21}$,
(c) $CO_2$R$^{5a}$,
(d) CON(R$^5$)$_2$,
(e) S(O)$_x$-($C_1$–$C_4$)-alkyl, or
(f) N($CH_2CH_2$)$_2$Q; and R$^{24}$ is:
(a) ($C_1$–$C_4$)-alkyl,
(b) CHR$^{25}$-O-COR$^{26}$,
(c) $CH_2CH_2$-N[($C_1$–$C_2$)-alkyl]$_2$,
(d) $CH_2CH_2$-N[$CH_2CH_2$]$_2$O,
(e) ($CH_2CH_2O$)$_y$-O-[($C_1$–$C_4$)-alkyl], wherein y is 1 or 2,
(f) aryl, or —$CH_2$-aryl, where aryl is as defined above or optionally substituted with —$CO_2$-($C_1$–$C_4$)-alkyl,

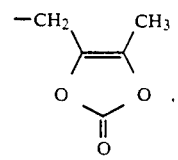
(g)

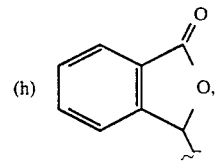
(h)

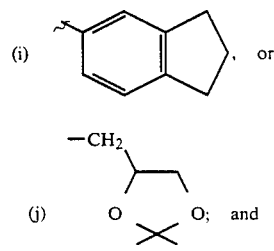
(i), or (j) —$CH_2$ ... O O; and

R$^{25}$ and R$^{26}$ independently are ($C_1$–$C_6$)-alkyl or phenyl.

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which ar modified so that each contains a carbon to carbon double bond or triple bond, respectively, such as vinyl, allyl and 2-butenyl.

Cycloalkyl denotes rings composed of 3 to 8 methlene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

GENERAL METHODS FOR PREPARATION OF COMPOUNDS OF GENERAL FORMULA I

The methods described below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by Formula I and a substituted benzyl substituent which is attached to the heterocyclic component through an oxygen atom. Thus, two generally applicable approaches to antagonists of formula I are these:

1. A substituted quinolone or azaquinolone is prepared as described below in Part I. The quinolone or azaquinolone is then alkylated at a nitrogen atom with a substituted benzyl halide or pseudohalide giving an O-alkylated quinolineor azaquinoline as described in the Schemes below, this alkylating agent is often designated as "ArCH$_2$-Q" where Q is a halide (—Cl, Br, I) or pseudohalide (—OMs, OTs, OTf). In some cases, alkylation may take place at both the oxygen and nitrogen atoms of the pyridine ring, and in these cases, separation by fractional crystallization or by chromotographic methods may be necessary for isolation of the desired product. In some cases, the alkylation step produces a fully-assembled antagonist of Formula I, except that functional groups on the alkylating agent or on the quinoline or azaquinoline moiety may be present in protected form and require deprotection steps to be carried out to complete the synthesis. In other cases, the alkylation is carried out with a substituted benzylic halide or pseudohalide ("ArCH$_2$-Q"), but here the alkylation step is followed by subsequent steps which are required to assemble the substituted benzyl element of the antagonist of Formula I. The alkylation steps and subsequent steps used to prepare antagonists of formula I, are described below.

2. In another approach to antagonists of formula I, a substituted benzyl element is introduced at the beginning and synthetic routes of this type are illustrated below. In most cases where this general approach is used, the substituted benzyl component which is introduced during the synthesis of the heterocycle must be subjected to further synthetic transformations in order to complete the synthesis of the antagonist of Formula I. In the Schemes shown below, this substituted benzyl component is designated as "—CH$_2$Ar," and is usually introduced by an alkylation step with a substituted benzyl halide or pseudohalide designated ArCH$_2$-Q (where Q is, for example, Cl, Br, I, F, OTs, or OMs). Substituted benzyl halides or pseudohalides which are useful in the preparation of alkylated quinolines or azaquinolines described are illustrated by those listed below in Table 1. In cases where these benzylic halides and pseudohalides are not commercially available, they are prepared as described below or by standard methods of organic synthesis. Subsequent steps which may be required to complete the synthesis of antagonists of Formula I are described below.

The compounds of this invention maybe resolved using the techniques known in the art. The diastereomeric salts and esters of the enantiomers are separated and the desired compound is the more active stereoisomer. The compounds of this invention, their pharmaceutically acceptable salts and their prodrug forms are included within the scope of this invention.

TABLE 1

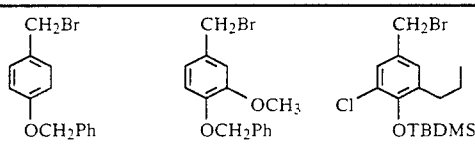

TABLE 1-continued

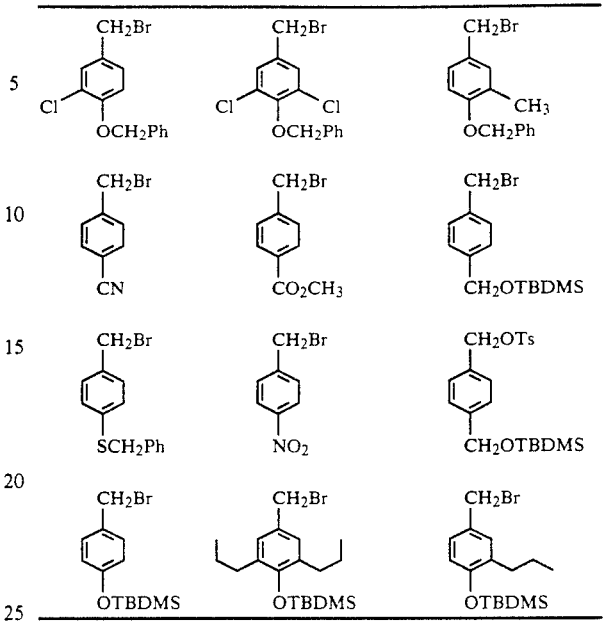

Abreviations used in schemes and examples are listed in Table 2.

TABLE 2

| Reagents | |
|---|---|
| NBS | N-bromosuccinimide |
| AIBN | Azo(bis)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |
| DIPEA | Diisopropylethylamine |
| TBS-Cl | Tributylsilyl chloride |
| TBAF | tetrabutylammonium fluoride |
| TMSCN | trimethylsilyl cyanide |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| HMPA | hexamethylphosphoramide |
| Others: | |
| Phe | phenylalanine |
| rt | room temperature |
| TBDMS | t-butyldimethylsilyl |
| OTf | OSO$_2$CF$_3$ |
| Ph | phenyl |
| FAB-MS (FSBMS) | Fast atom bombardment mass spectroscopy |
| NOE | Nuclear Overhauser Effect |
| SiO$_2$ | silica gel |
| trityl | triphenylmethyl |
| Bn | benzyl |

PART I: Preparation of the quinol-4-ones and 1,5-azaquinol-4-ones of Formula II Formula II

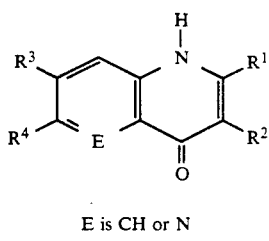

E is CH or N

The compounds of Formula II can be prepared using the synthetic routes shown below in Schemes I-1 and I-2. Scheme I-1 describes the Conrad-Limpach synthesis [Chem. Ber, 21, 523 (1988)] a straight forward route to quinol-4-ones. The 1,5-azaquinol-4-ones can be prepared by an analogous route as shown in Scheme I-2. Recent EPO and PCT publications, EP 412,848 and WO 91/07404, by ICI describe the preparation of the quinol-4-ones and 1,5-azaquinol-4-ones, respectively.

SCHEME I-1

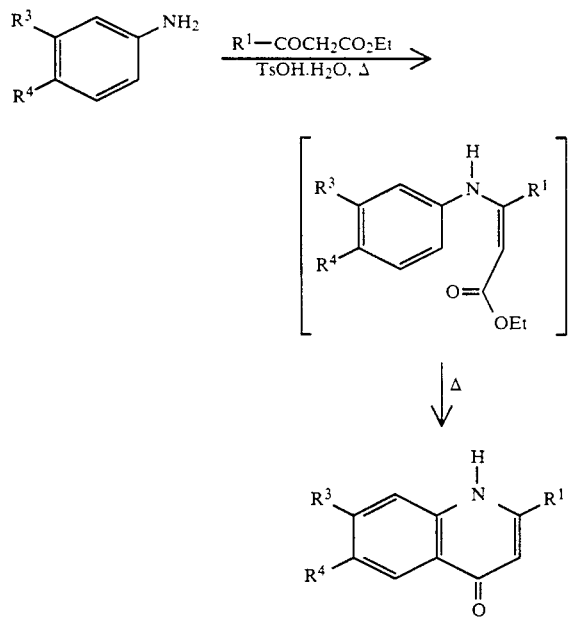

SCHEME I-2

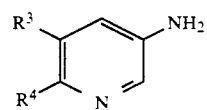

SCHEME I-2 (continued)

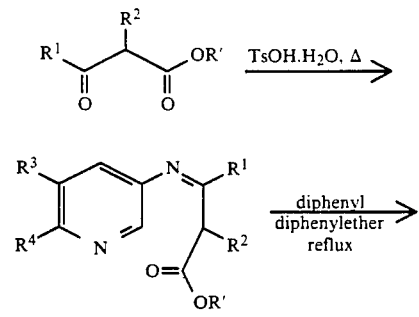

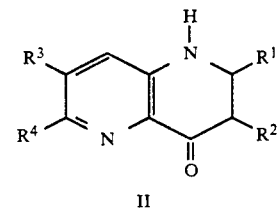

II

PART II: Preparation os substituted benzyl derivatives of the general Formula I The synthesis of Angiotensin II Antagonists incorporating a substituted benzyl group as shown in Formula I may be accomplished by reaction of the appropriate quinolone or azaquinolone with a benzylic compound bearing a good leaving group, in the presence of a base, and the appropriate substituents on the benzylic group $R^9$, $R^{10}$, $R^{11}$, $R^{12}$, X, Y and Z as shown in Formula I. Alternatively, compounds with structures according to Formula I may also be synthesized in stages from a benzyl-substituted quinoline or azaquinoline which contains the substituents $R^9$, $R^{10}$ and X, followed by reaction with an intermediate (such as a substituted alpha-bromophenylacetic ester) which introduces the substituents at $R^{11}$, $R^{12}$ and Z. Examples of this latter methodology in which a benzyl-substituted heterocyclic intermediate is prepared first, and then elaborated to afford compounds with structures described by Formula I, are shown in the Schemes II-1, II-2 and II-3. The preparation of compound 5 of Formula I wherein: $R^9$, $R^{10}$ and $R^{11}$ are H, X=O, Y=a single bond, Z=$CO_2$H and $R^{12}$=phenyl appears in Scheme II-1. Deprotonation of a substituted quinolone or azaquinolone with bases such as sodium hydride or potassium carbonate in DMF followed by alkylation with 4-t-butyldimethylsilyloxy-benzyl bromide may afford the protected ether 2. The silyl protecting group may be removed by treatment with tetrabutylammonium fluoride to afford the intermediate phenol 3. The phenol 3 can be treated with an appropriate base (NaH or KH/18-crown-6 or $K_2CO_3$) in DMF and then alkylated with substituted methyl 2-bromophenylacetate to furnish ester 4, which after hydrolysis may provide the free acid 5.

SCHEME II-1

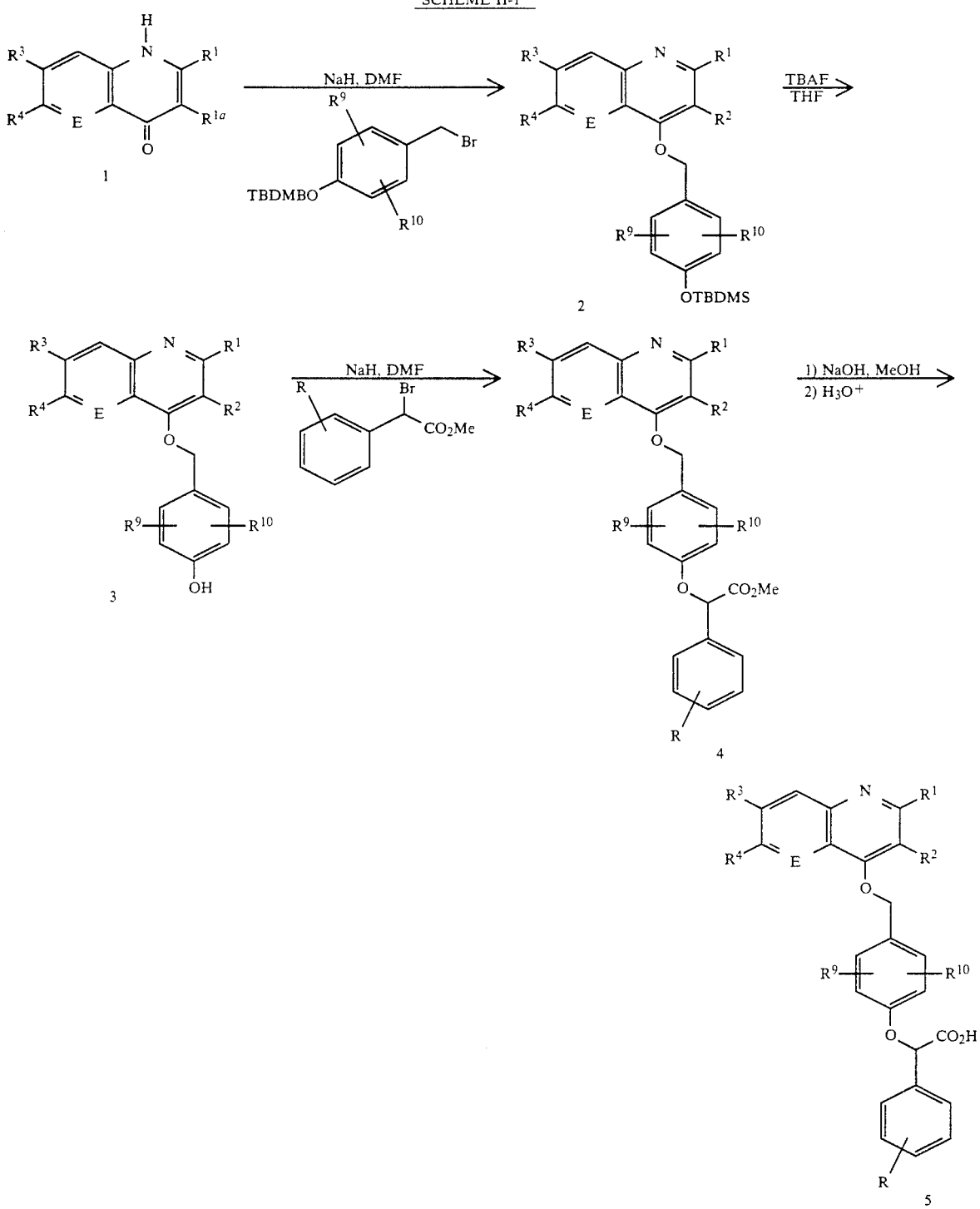

Substituted 2-bromophenylacetic esters are typically employed in the synthesis of compounds of general Formula I when it is desired that $R^{12}$ be a substituted phenyl group, $R^{11}$ is hydrogen, Y is a single bond and Z is a carboxylic acid. These substituted 2-bromophenylacetic esters are readily prepared from substituted phenyl acetic acids (6) by a Hell-Volhard-Zelinsky reaction as shown in Scheme II-2. Alternatively, substituted 2-bromophenylacetic esters may also be obtained from benzaldehydes (8) as shown in Scheme II-3. Reaction of the substituted benzaldehydes (8) with trimethylsilyl cyanide affords the trimethylsilyl-cyanohydrins 9. Treatment of 9 with acidic ethanol produces the hydroxy esters 10, and subsequent reaction with carbon tetrabromide and triphenylphosphine provides the substituted 2-bromophenylacetic esters 7.

SCHEME II-2

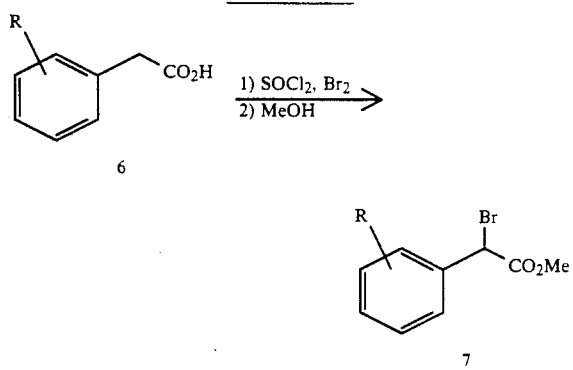

SCHEME II-3

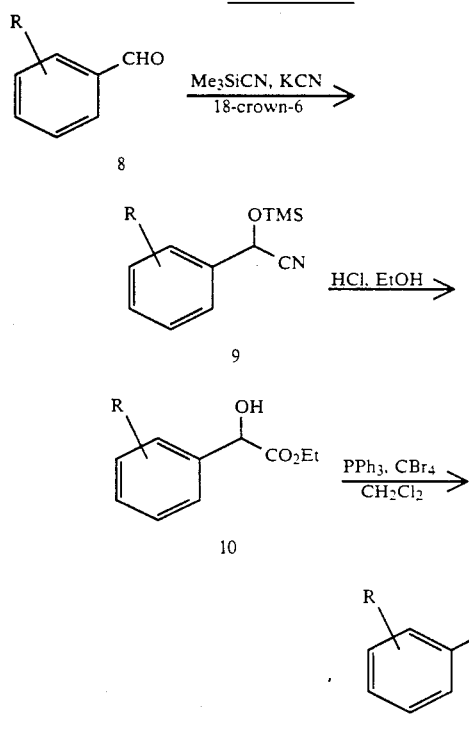

SCHEME II-4

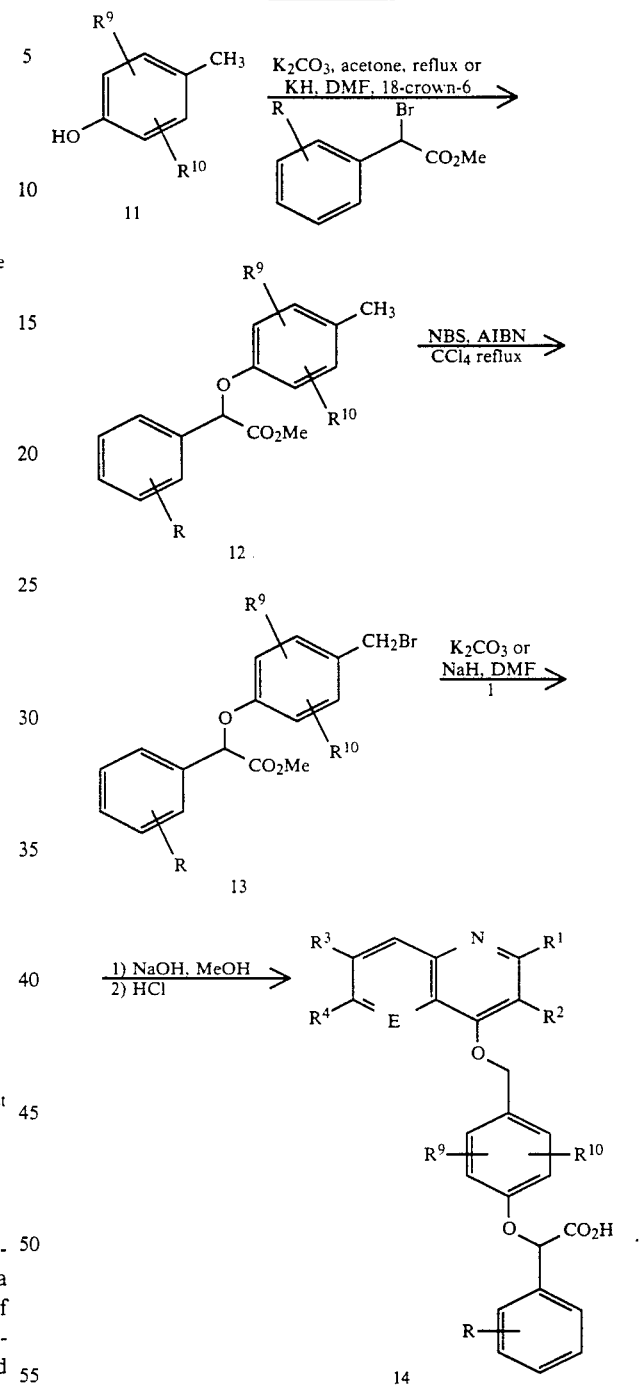

The synthesis of Angiotensin II Antagonists incorporating a substituted benzyl element defined by Formula I may also be accomplished by the alkylation reaction of an appropriate quinolone or azaquinolone with a benzylic intermediate bearing a good leaving group, and with all of the appropriate substituents $R^9$, $R^{10}$, $R^{11}$, $R^{12}$, X, Y and Z in place. This approach, which is generally preferred when either $R^9$ or $R^{10}$ are non-hydrogen, is illustrated in Scheme II-4. Deprotonation of p-cresol (11) with strong bases such as potassium hydride or potassium tert-butoxide in DMF and alkylation with methyl 2-bromo-2-phenylacetate gives the ether 12. Bromination of 12 at the benzylic methyl group with N-bromosuccinimide gives the alkylating agent 13. Deprotonation of the heterocycle (1) with sodium hydride in DMF, followed by reaction with bromide 13, and subsequent ester hydrolysis may provide the acid 14.

A strategy similar to that of Scheme II-4 is applied when substitution at $R^{11}$ is desired as shown in Scheme II-5. Intermediate ethers such as 12 in Scheme II-6 are deprotonated with strong bases such as lithium bis(trimethylsilyl)amide in THF and can then be reacted with an alkylating agent such as an alkyl halide or mesylate. In this case, reaction of the anion derived from ether 12 with methyl iodide affords the alkylated product 15. Reaction of 15 with N-bromosuccinimide gives bromide 16, which may in turn be used for alkylation of the appropriate heterocycle to provide 17.

SCHEME II-5

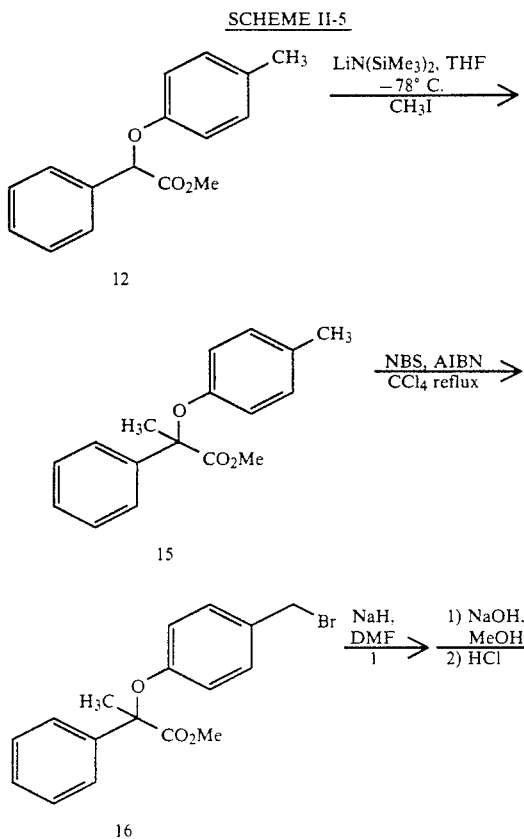

SCHEME II-6

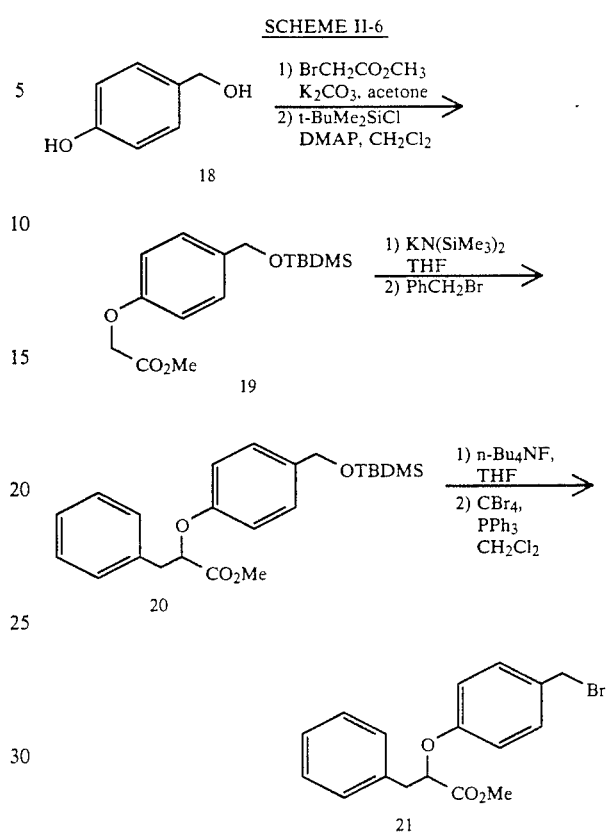

The synthesis of the alkylating agent 31 is shown in Scheme II-6. In this example, p-hydroxybenzyl alcohol (18) is selectively alkylated at the phenolic hydroxyl group with methyl bromoacetate when they are refluxed with potassium carbonate in acetone. After the remaining hydroxyl group is protected as a tert-butyldimethylsilylether, this ether (19) is then be deprotonated with a strong base such as potassium bis(-trimethylsilyl)-amide and reacted with an alkylating agent in a manner similar to that shown for intermediate 12 in Scheme II-5. Alkylation of ether 19 with benzyl bromide provides 20. Desilylation of 20 and bromination of the resulting alcohol affords an alkylating agent 21.

Scheme II-7 illustrates the preparation of the alkylating agent 35. In this example, the Hell-Volhard-Zelinsky reaction converts 4'-methylphenylacetic acid (23) to the alpha-bromoester 24, which is in turn reacted with the potassium salt of phenol to yield 25. Benzylic bromination of 25 provides alkylating agent 26.

SCHEME II-7

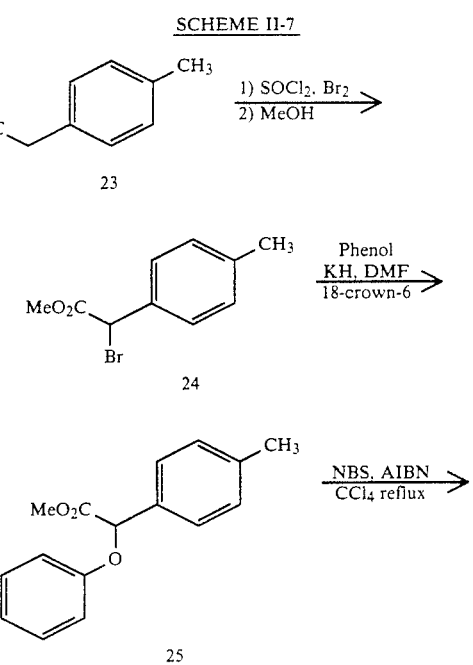

-continued
SCHEME II-7

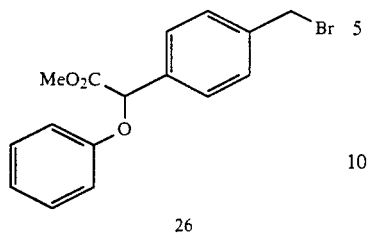

26

Scheme II-8 illustrates the preparation of benzyl bromide 41. A Reformatsky reaction is first employed to prepare methyl 3-hydroxy-3-(4-methylphenyl)-2-phenyl-propanoate (29) from the starting materials shown in Scheme II-8. When heated in the presence of p-toluenesulfonic acid in benzene 29 is dehydrated to the trans-stilbene derivative 30, and then benzylic bromination of 30 gives the alkylating agent 31 which may be used to prepare the antagonists of Formula I as described earlier in Scheme II-4.

-continued
SCHEME II-8

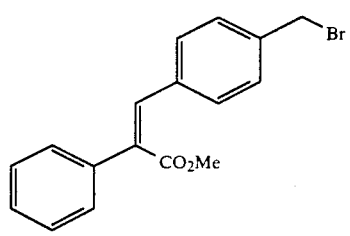

31

The possible synthesis of compound 34 of Formula I where Z is a tetrazol-5-yl group, is illustrated in Scheme II-9. Exposure of ester 32 to excess ammonia in methanol may produce the corresponding amide which upon dehydration with phosphorous oxychloride and triethylamine may give the nitrile 33. Reaction of the nitrile 33 with trimethylstannyl azide in refluxing toluene may then provide the tetrazole derivative 34.

SCHEME II-8

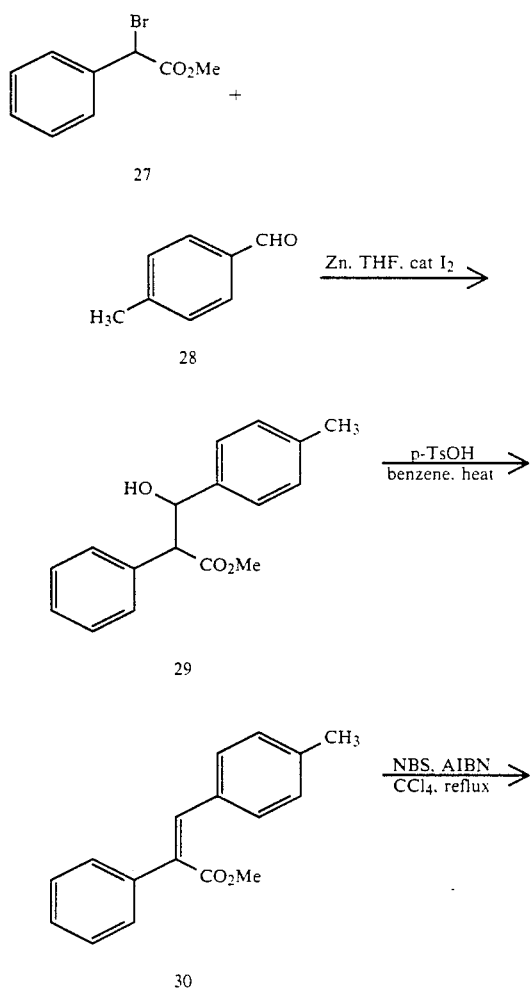

SCHEME II-9

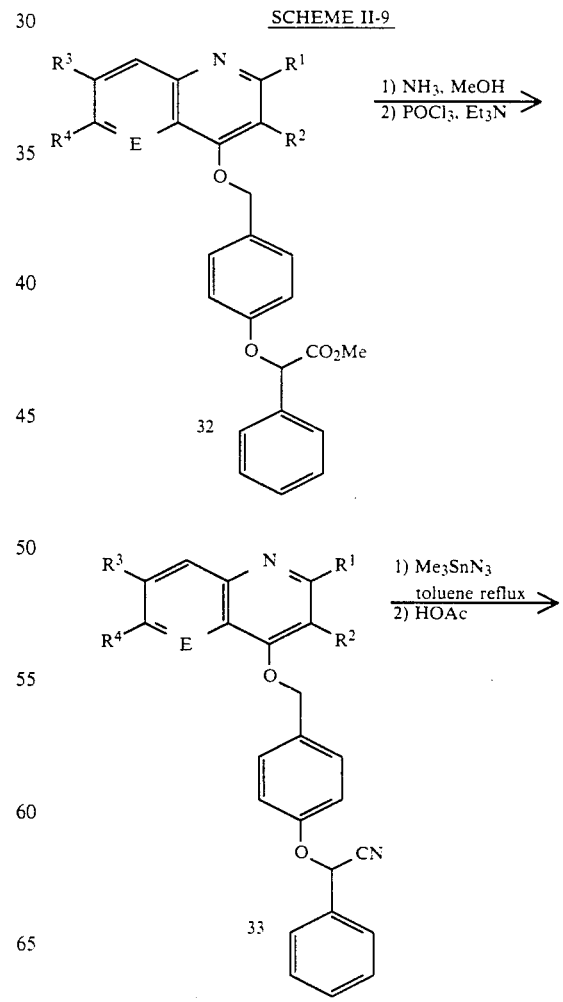

-continued
SCHEME II-9

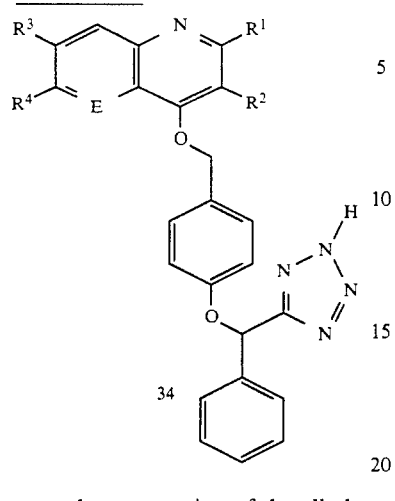

Scheme II-10 illustrates the preparation of the alkylating agent 39. In this synthesis, the ester group of intermediate 35 is converted to a nitrile prior to alkylating a substituted quinolone or azaquinolone (Part I) with this substituted benzyl element. Thus, reaction of ester 35 with ammonia in methanol, followed by dehydration of amide 36 produces nitrile 37. Benzylic bromination affords 38, which may then be reacted with the sodium salt of heterocycle 1 in DMF to give an intermediate which can be further transformed into the desired antagonist of formula I, as described in Scheme II-9.

SCHEME II-10

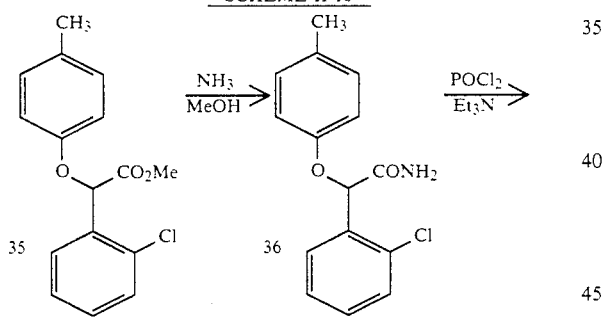

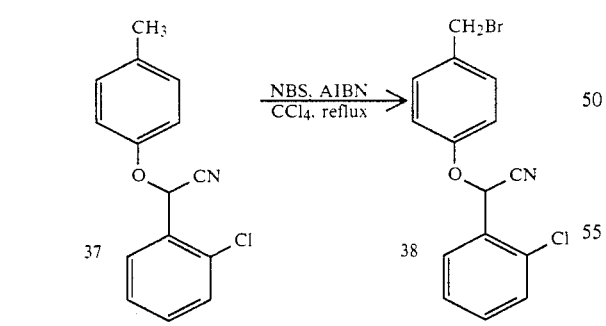

The preparation of the alkylating agent 55 is shown in Scheme II-12. In this synthesis, phenylacetonitrile is deprotonated with lithium bis(trimethylsilyl)amide and then alkylated with bromide 42 (preparation of bromide 42 is shown in Scheme II-11) to yield nitrile 43. The silylether group in compound 43 is directly converted to the bromide 45 by treatment with carbon tetrabromide, triphenylphosphine and acetone in dichloromethane (Mattes, H.; Benezra, C. Tetrahedron Lett., 1987, 1697). Alkylation of the sodium salt of quinolone or azaquinolone 1 with bromide 45, followed by reaction of 46 with trimethylstannyl azide in refluxing toluene, may yield the tetrazole 47.

SCHEME II-14

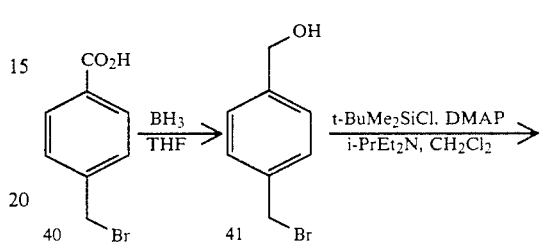

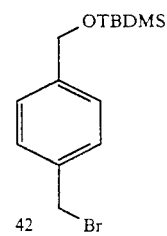

SCHEME II-12

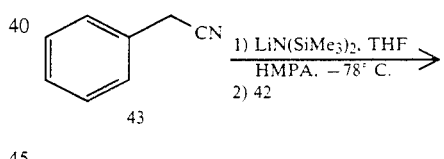

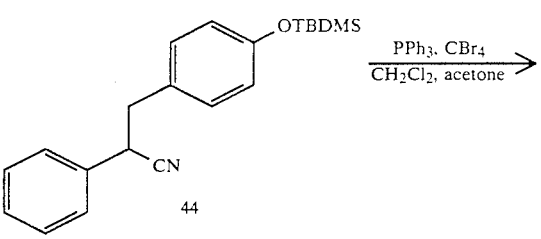

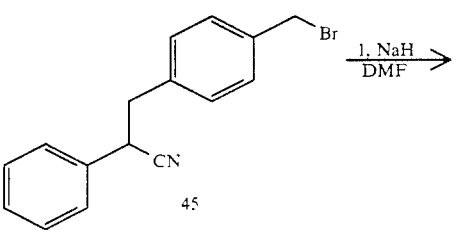

-continued
SCHEME II-12

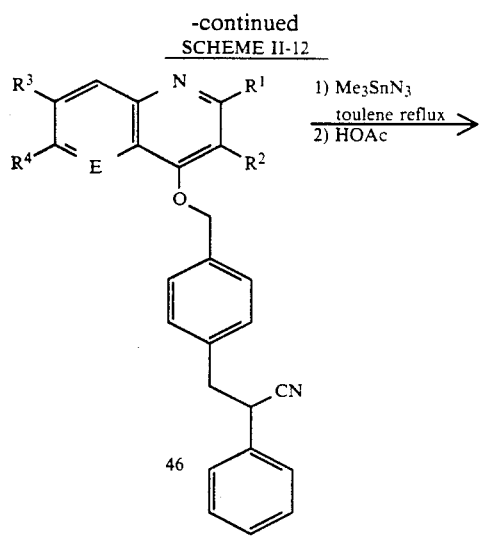

-continued
SCHEME II-13

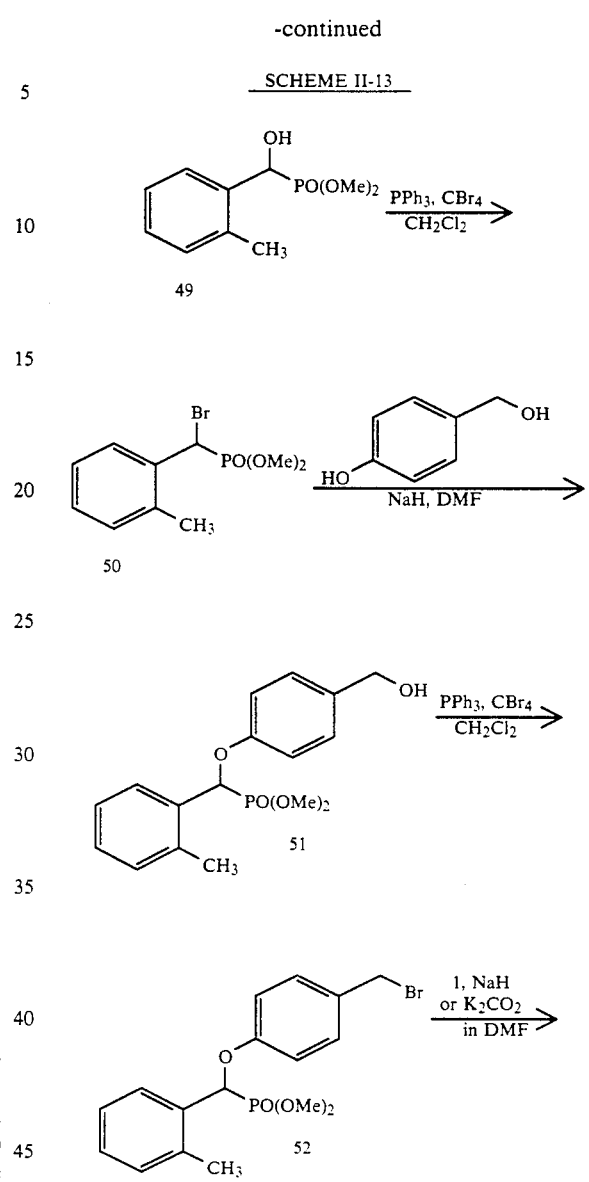

Scheme II-13 illustrates the preparation of a derivative of Formula I where $R^9$, $R^{10}$ and $R^{11}$ are H, X=O, Y=a single bond, $R^{12}$ is 2-methylphenyl, and Z is a phosphonic acid group. Reaction of o-tolualdehyde (48) with dimethylphosphite in the presence of triethylamine affords the phosphonate ester 49. Bromination of the hydroxyl group of 49 with carbon tetrabromide and triphenylphosphine in dichloromethane gives bromide 50. Deprotonation of p-hydroxybenzyl alcohol with sodium hydride in DMF followed by addition of bromide 50 affords intermediate 51. A second bromination reaction (CBr₄, PPh₃, CH₂Cl₂) converts alcohol 51 to the bromide 52 which may then be used to alkylate the quinolone or azaquinolone under standard conditions to give the phosphonate mono-ester 53. Phosphonic acid 54 may be obtained by treatment of ester 53 with trimethylsilyl bromide.

SCHEME II-13

-continued
SCHEME II-13

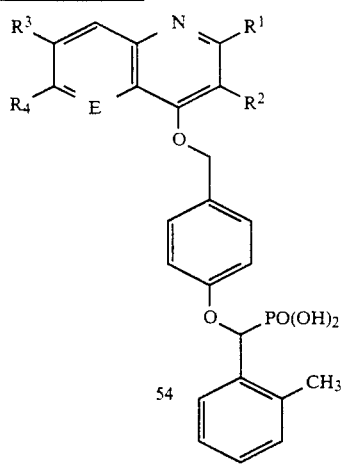

The possible synthesis of a derivative of Formula I where Z is an acyl-sulfonamide group is illustrated in Scheme II-14. Reaction of acid 5 (Scheme II-1) with 1,1'-carbonyldiimidazole in THF at elevated temperatures gives an acylimidazolide which may be reacted with a sulfonamide (benzenesulfonamide in this example) and DBU in THF to provide the target compound (55) where Z is the acyl-sulfonamide group.

SCHEME II-14

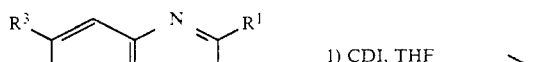

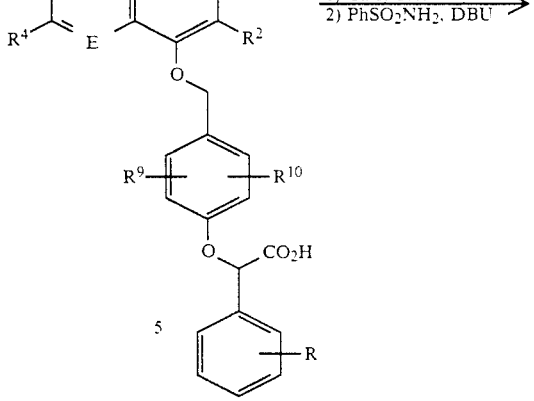

A variety of 2-substituted phenols are selectively carboxylated when refluxed with carbon tetrachloride, 50% aqueous sodium hydroxide and powdered copper (European Patent Application #193,853, Sep. 10, 1986) to afford the corresponding substituted 4-hydroxybenzoic acids. This reaction may be added to the synthetic sequence when it is convenient to derive the desired substituent on the benzyl portion of the target AII Antagonist from a readily available 2-substituted phenol. This strategy is illustrated for the preparation of the alkylating agent 59 shown in Scheme II-15. Carboxylation of 2-ethylphenol provides 3-ethyl-4-hydroxybenzoic acid (57). Acid 57 is then esterified, silylated, reduced and desilylated to give the 3-ethyl-4-hydroxybenzyl alcohol 58. Alcohol 58 may then be transformed into 59, which may then be used to complete the synthesis of corresponding AII Antagonist of formula I using the previously discussed methodology.

SCHEME II-15

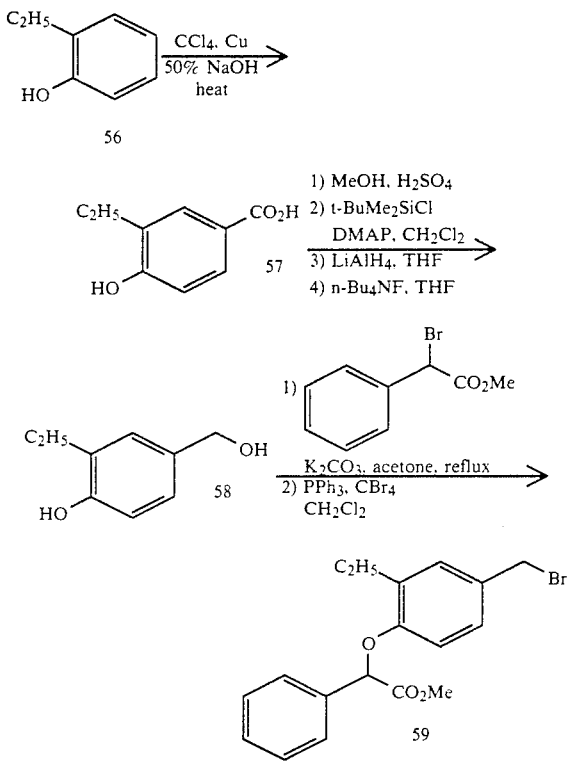

The Claisen rearrangement of phenylallylethers offers another useful technique for the introduction of alkyl substitutents ($R^9$ or $R^{10}$) at the meta position of the substituted benzyl element. In Scheme II-16, Claisen rearrangement the allyl ether 60 in refluxing dichlorobenzene provides the hydroxy allyl benzoate 61. Silylation of the phenol (61), followed by reduction of the ester group and bromination of the alcohol leads to the benzyl bromide 62. Alkylation of the heterocycle (1) followed by desilylation may provide intermediates related to 63. Alkylation of 63 with methyl 2-bromophenylacetate followed by alkaline hydrolysis may give a derivative of Formula I (64) wherein $R^9$ is a meta-allyl group. Hydrogenation of intermediate 63 followed by the same sequence of reactions could provide derivative 65 where $R^9$ is the meta-propyl group as shown in Scheme II-16. Alternatively, the allyl side chain of 61 can be reduced to the n-propyl group under catalytic hydrogenation.

SCHEME II-16

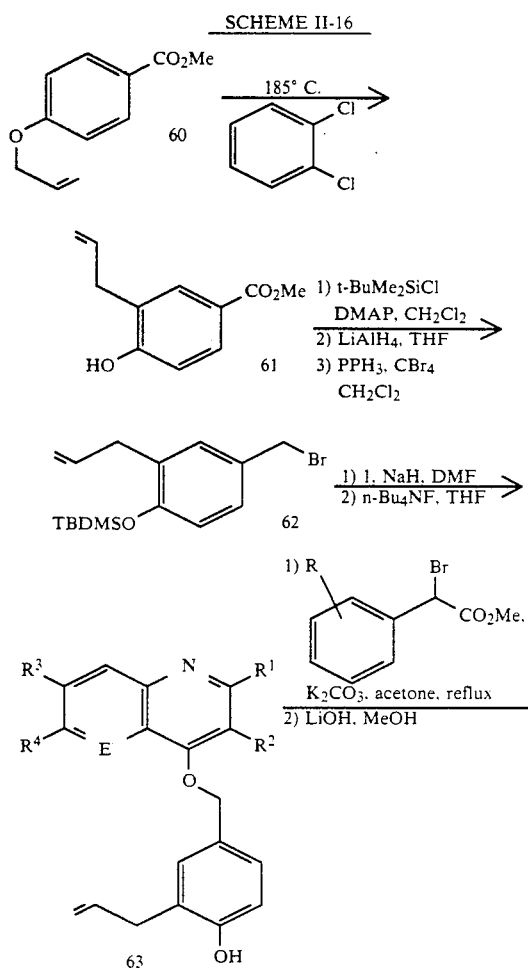

-continued
SCHEME II-16

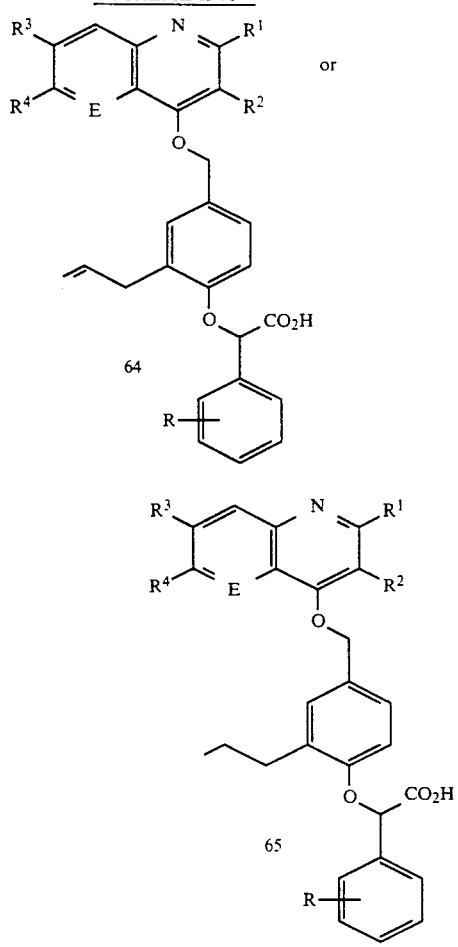

The Claisen rearrangement strategy for the introduction of a meta-alkyl substituent onto the substituted benzyl element of an AII Antagonist of Formula I may be exercised twice when it is desired that both $R^9$ and $R^{10}$ be meta-alkyl substituents. Thus, allyl phenol 61 may be converted to its O-allylether and subjected to a second Claisen rearrangement to provide the phenol (66) shown in Scheme II-17. Silylation of phenol 66, followed by catalytic hydrogenation and reduction of the ester group with lithium aluminum hydride gives the benzyl alcohol 67. A Mitsunobu reaction of the benzyl alcohol 67 with a quinolone or azaquinolone (1) described in Part I, followed by deprotection of the silylether may provide an intermediate related to 68. The phenolic hydroxyl group of 68 may then be alkylated with a substituted alpha-bromoester and the ester hydrolyzed to yield the acid 69 in which $R^9$ and $R^{10}$ are meta-propyl groups as shown in Scheme II-17.

SCHEME II-17

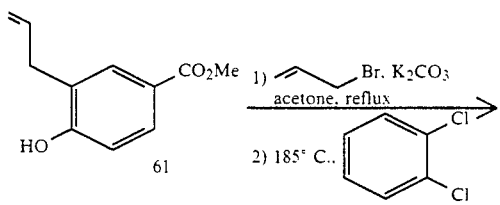

SCHEME II-17

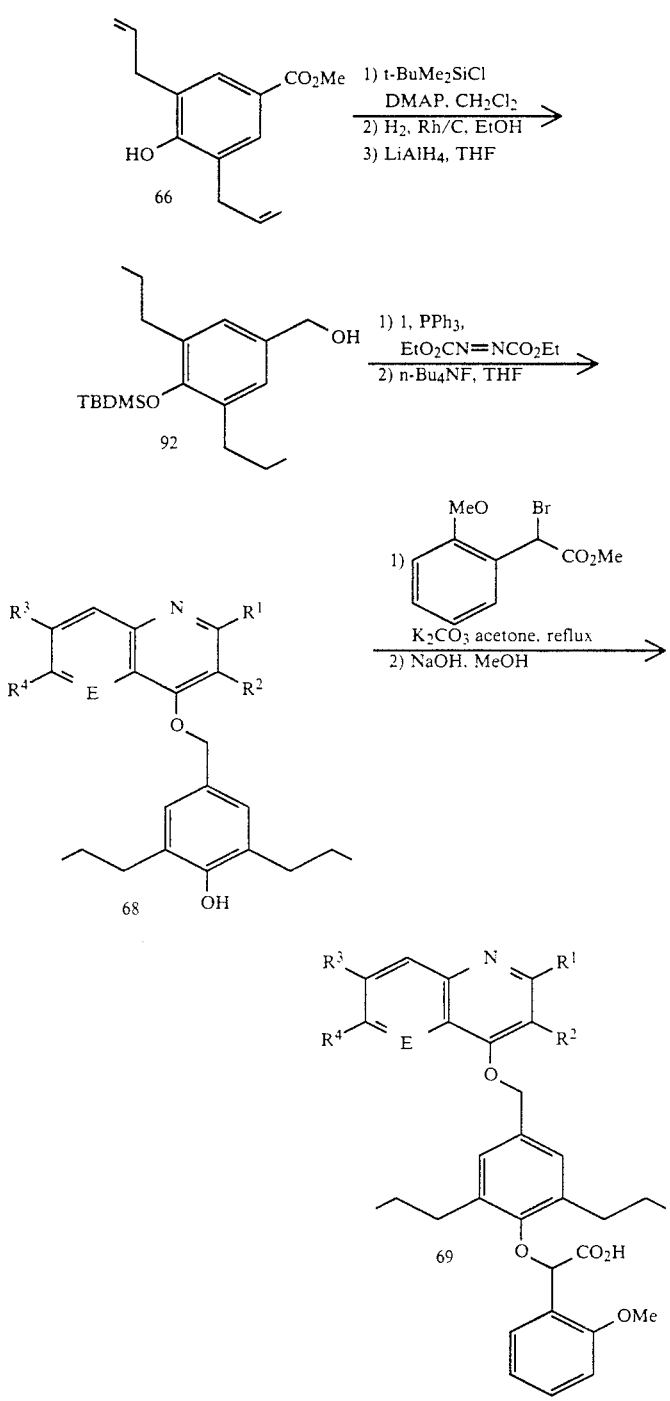

The synthesis of compounds of Formula I wherein: $R^9$, $R^{10}$ and $R^{11}$ are H, Y= a single bond, Z= $CO_2H$ $R^{12}$= phenyl, and X= $NR^{13}$, are presented in the following two Schemes. To access these analogs, quinolone or azaquinolone (1) defined in Part I may be alkylated with p-nitrobenzyl bromide to yield nitro compounds such as 70 in Scheme II-18. Catalytic hydrogenation of the nitro group or reduction of the nitro group with $SnCl_2$ or Fe provides the aniline derivative (71) which is then alkylated by an alpha-bromoester. The ester 72 is subsequently hydrolyzed to afford a derivative of Formula I (73) where X= NH.

SCHEME II-18

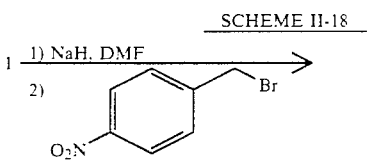

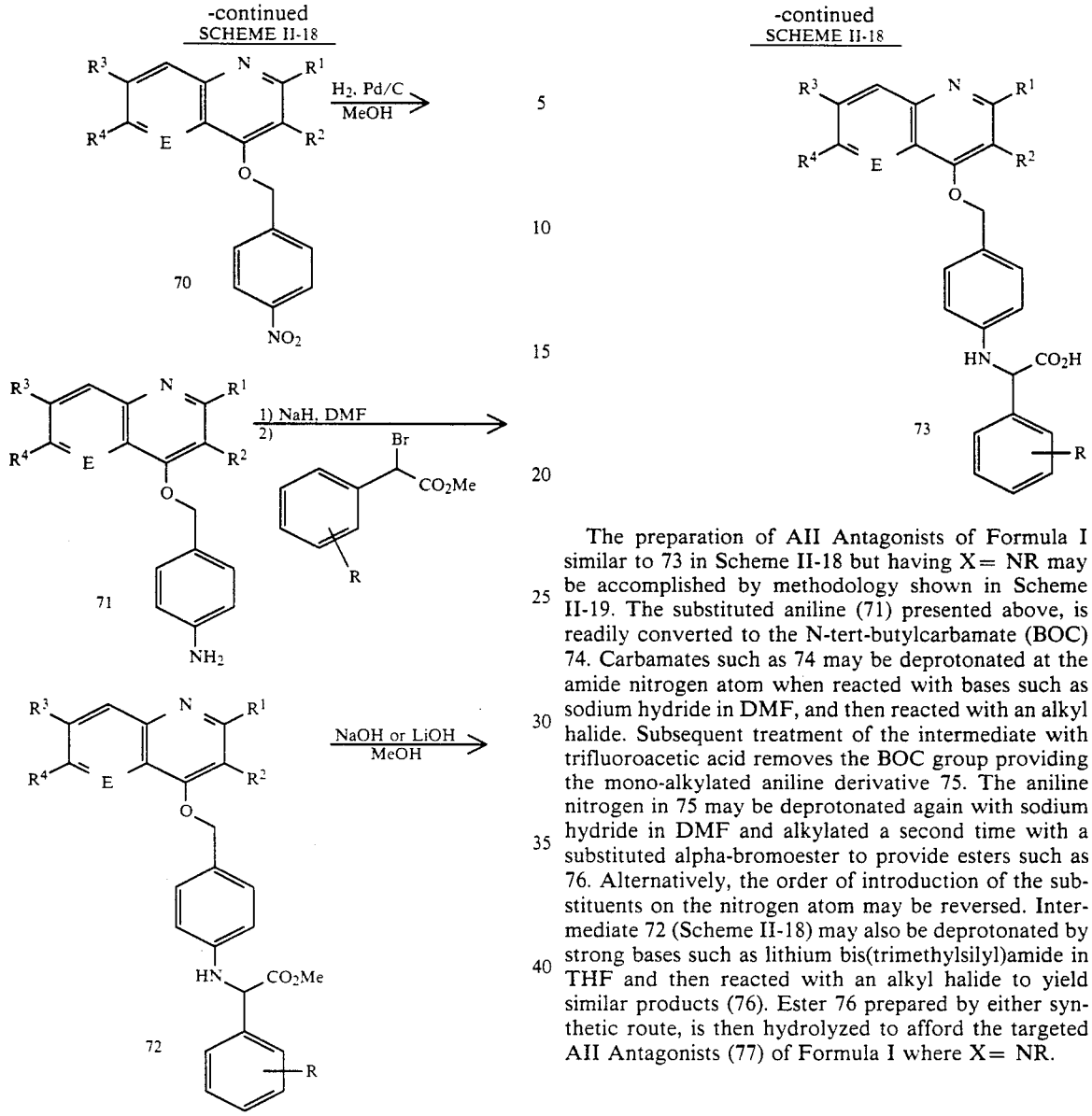

The preparation of AII Antagonists of Formula I similar to 73 in Scheme II-18 but having X= NR may be accomplished by methodology shown in Scheme II-19. The substituted aniline (71) presented above, is readily converted to the N-tert-butylcarbamate (BOC) 74. Carbamates such as 74 may be deprotonated at the amide nitrogen atom when reacted with bases such as sodium hydride in DMF, and then reacted with an alkyl halide. Subsequent treatment of the intermediate with trifluoroacetic acid removes the BOC group providing the mono-alkylated aniline derivative 75. The aniline nitrogen in 75 may be deprotonated again with sodium hydride in DMF and alkylated a second time with a substituted alpha-bromoester to provide esters such as 76. Alternatively, the order of introduction of the substituents on the nitrogen atom may be reversed. Intermediate 72 (Scheme II-18) may also be deprotonated by strong bases such as lithium bis(trimethylsilyl)amide in THF and then reacted with an alkyl halide to yield similar products (76). Ester 76 prepared by either synthetic route, is then hydrolyzed to afford the targeted AII Antagonists (77) of Formula I where X= NR.

SCHEME II-19

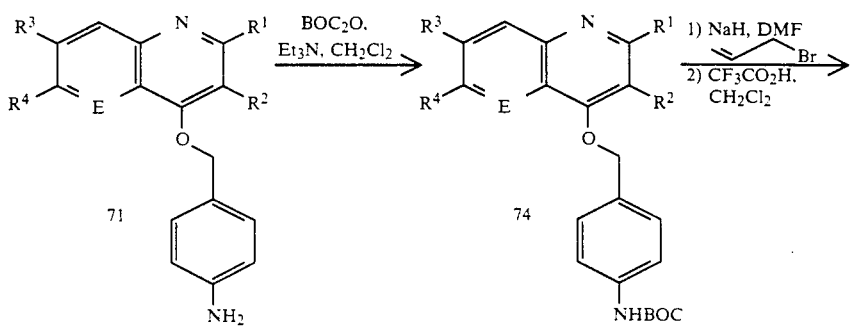

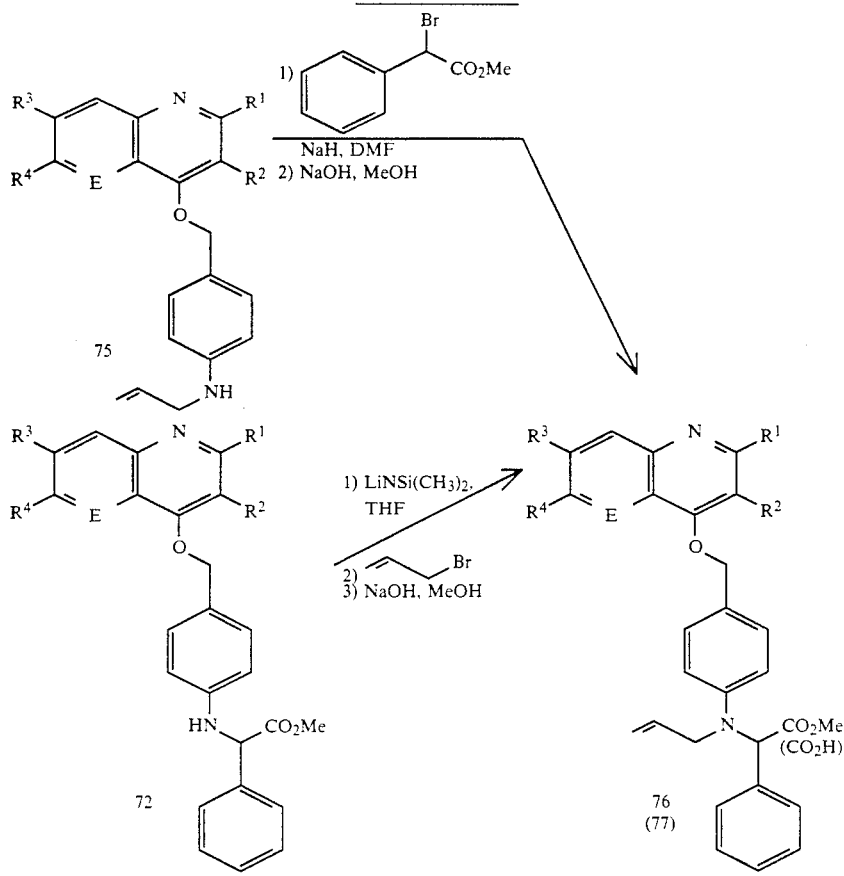

SCHEME II-19

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306-326), H. Ferres, *Drugs of Today*, Vol. 19, 499-538 (1983) and *J. Med. Chem.*, 18, 172 (1975). Examples of such prodrugs include the physiologically acceptable and metabolically labile ester derivatives, such as lower alkyl (e.g. methyl, or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}I$-Sar$^1$Ile$^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-Sar$^1$Ile$^8$-angiotensin II was presented as a measure of the efficacy of such compounds as AII antagonists.

RECEPTOR ASSAY USING BOVINE ADRENAL CORTEX PREPARATION

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3H$-angiotensin II was presented as a measure of the efficacy of such compounds as AII antagonists.

Using the methodology described above, representative compounds of the invention were evaluated and were found to exhibit an activity of at least $IC_{50}<50$ mM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the intermediates of compounds of Formula I and as such are not to be considered as limiting the invention set forth in the claims appended hereto.

EXAMPLE 1

Methyl 4-(bromomethyl)benzoate

To a solution of 1.0 eq of 4-(bromomethyl)benzoic acid in 20 ml of methanol and 50 ml of toluene; was added dropwise 2.05 eq of trimethylsilyldiazomethane while stirring at room temperature. The reaction was titrated until a persistant pale yellow color existed from the addition of excess trimethylsilyldiazo- methane. Let stir at room temperature for 1 hr to insure the complete evolution of N₂. Thin layer chromatography in 1:1 hexane:ethyl acetate indicated the disappearance of starting material and the appearance of desired ester with an Rf of 0.7.

FAB-MS M+H=230, 228.

¹H NMR (300 mHz, CDCl₃, ppm) δ8.02 (d, 2H); 7.46 (d, 2H); 4.50 (s, 2H); 3.93 (s, 3H)

EXAMPLE 2

Methyl-2-amino-3-phenyl-2-phenylmethypropionate

Step A: Preparation of N-benzylidene-D-phenylalanine methyl ester

To a suspension of 1.0 eq D-phenylalanine HCl (1.6 g, 7.4 mmol) was added 1.0 eq triethylamine to dissolve the D-phenylalanine. To this solution was added 1 equiv. of MgSO₄ followed by the addition of 1.0 eq benzaldehyde, the reaction was stirred overnight at room temperature under N₂ atmosphere. The reaction mixture was sripped of solvent and pumped on the residue contained a good deal of triethylamine hydrochloride which was removed by dissolving the product in THF and filtering out the TEA.HCl. The crude benzylidene looked fine by NMR and was all taken on in the next step.

¹H NMR: (300 mHz, CDCl₃, ppm) 7.90 (s, 1H); 7.68 (d, 2H); 7.4 (m, 3H); 7.26–7.12 (m, 5H); 4.17 (m, 1H); 3.72 (s, 3H); 3.38 (dd, 1H), 3.15 (dd, 1H).

Step B: Preparation of Methyl-2-amino-3-phenyl-2-phenylmethypropionate

To a solution of the benzylidene, Step A, in 25 ml dry THF at −78° C. was added 1.05 eq of 1.0M lithium hexamethyldisilylazide in THF (7.8 ml) over 10 minutes. After 30 minutes, a solution of 1.05 eq benzyl bromide in 15 ml THF was added over 15 minutes. The reaction mixture was stirred at −70° C. for 15 min. and then gradually warmed to −40° to −35° C. and stirred at this temperature for 1.5 hours, after which the reaction appeared to be complete. The reaction mixture was quenched at −35° C. by the addition of 50 ml of 1.0N HCl and it was then allowed to warm to room temperature with stirring. The reaction mixture was then extracted twice with hexane to remove the bezaldehyde which had been formed. The aqueous layer was then extracted three times with ethyl acetate, and the combined extracts were washed with saturated NaHCO₃ and brine, then dried over MgSO₄. The solvent was removed in vacuo to give 324 mg of a yellow crystalline solid. The pH of the aqueous layer was adjusted from 1.4 to 11.8 using 3N NaOH producing a milky white solution, which became clear upon addition of ethyl acetate. The basic aqueous layer was extracted twice more with ethyl acetate, and the combined extracts were washed with brine and dried over MgSO₄. The solvent was removed in vacuo to give a colorless oil (1.37 g) giving a total yield of 85%. FAB-MS: M+H=270

¹H NMR: (300 mHz, CDCl₃, ppm); δ7.3–7.15 (m, 10H); 3.65 (s, 3H); 3.37 (d, 2H); 2.74 (d, 2H).

EXAMPLE 3

Methyl 2-(4-bromomethylphenoxy)-2-(2'-chlorophenyl)acetate

Step A: Preparation of Methyl 2-bromo-2'-chlorophenylacetate o-Chlorophenylacetic acid (5.00 g, 29.3 mmol) and thionyl chloride (2.67 ml, 36.6 mmol) are heated to reflux. Bromine (1.51 ml, 29.3 mmol) was added dropwise over 10 minutes and continued to reflux for 17 hrs. The reaction was cooled to room temperature and 30 ml of CH₃OH was added slowly. The solvent was removed in vacuo and the residue chromatographed on silica gel eluting with 5% ethyl acetate in hexane. The product was isolated in a 28% yield (2.13 g).

¹H NMR (300 MHz, CDCl₃, ppm): 3.8 (s, 3H); 5.95 (s, 1H); 7.25–7.45 (m, 3H); 7.7–7.8 (m, 1H).

Step B: Preparation of Methyl 2-(4-methylphenoxy)-2-(2'-chlorophenyl)acetate

To a suspension of KH (0.53 g, 4.63 mmol) in 5 ml of DMF under N₂ at 0° C. was added p-cresol (0.5 g, 4.63 mmol). The reaction mixture was stirred until the evolution of H₂ was complete. Then 50 mg of 18-crown-6 ether was added, followed by the product of Example 3, Step A (1.22 g, 4.63 mmol) in 5 ml DMF. The reaction mixture was stirred at 0° C. for 30 minutes and then allowed to warm to room temperature. The reaction mixture was concentrated in vacuo and chromatographed on silica gel (130 mm×30 mm) eluting with 5% ethyl acetate in hexane. The product was isolated in a 77% yield (1.03 g).

FAB-MS: 290,292

¹H NMR (300 MHz, CDCl₃, ppm): δ2.25 (S, 3 HO 3.8 (S, 3H) 6.15 (S, 1H) 6.8–6.9 (d, 2H) 7.25–7.35 (m, 2H) 7.4–7.5 (m, 1H) 7.6–7.7 (m, 1H) 7.6–7.7 (m, 1H).

Step C: Preparation of Methyl 2-(4-bromomethylphenoxy)-2-(2'-chlorophenyl)acetate A solution of the product of Example 3, Step B (0.2 g, 0.69 mmol), N-bromosuccinimide (117 mg, 166 mmol) and a catalytic amount of AIBN in 2 ml CCl₄ was refluxed for 30 minutes. The reaction mixture was concentrated in vacuo and chromatographed on silica gel (125×20 mm) eluting with 5% ethyl acetate in hexane. The product was isolated in a 73% yield (186 mg).

FAB-MS: 368, 370, 372 (10:13:3 isotopic ratio due to the presence of a chlorine and a bromine).

¹H NMR (300 MHz, CDCl₃, ppm): 3.8 (s, 3H) 4.5 (S, 2H); 6.15 (s, 1H); 6.85–6.95 (d, 2H); 7.25–7.35 (m, 4H); 7.4–7.5 (m, 1H); 7.6–7.7 (m, 1H).

EXAMPLE 4

3-(4-Bromomethyl)phenyl-2-phenylpropionitrile

Step A: Preparation of 4-(bromomethyl)benzylalcohol

A suspension of 4-bromomethylbenzoic acid (5.04; 23.3 mmol) in THF (30 ml) was cooled to 0° C. and treated with borane/THF (35 mmol). The ice bath was removed and the mixture was allowed to warm to room temperature and stirred for 1.5 hours. The excess borane was quenched with MeOH, and then with water, and the reaction mixture was concentrated in vacuo. The residue was dissolved in ethyl acetate and washed with 4% HCl, water NaHCO₃, brine, dried (MgSO₄), filtered, concentrated in vacuo to afford 4.44 g (94%) of the title compound.

¹H NMR: (300 MHz, CDCl₃, ppm): 7.38 (q,4H); 4.70 (s,2H); 4.51 (s,2H).

FAB MS: m/e=202 (M+H).

Step B: Preparation of 4-(bromomethyl)-t-butyldimethylsilyloxymethylbenzene

To a solution of the product of Example 4 Step A, (4.44 g, 22.1 mmol) in CH$_2$Cl$_2$ was added N,N-diisopropylethyl amine (1.2 eq.) and 4-dimethylaminopyridine (0.1 eq.), and t-butyldimethylsilyl chloride (1.2 eq.). The mixture was stirred for 1.5 hours at room temperature, then concentrated in vacuo. The residue was dissolved in ethyl acetate and washed with water, brine, dried (MgSO$_4$), filtered, and concentrated in vacuo. The residue was chromatographed on silica (ethyl acetate/hexanes (2.5/97.5)) to afford 5.0 g (71%) of the title compound.

$^1$H NMR (300 MHz, CDCl$_3$, ppm): 7.34 (q,4H); 4.74 (s,2H); 4.59 (s,2H); 0.95 (s,9H); 0.11 (s,6H).

Step C: Preparation of 3-(4-t-butyldimethylsilyloxymethyl)phenyl-2-phenylpropionitrile A solution of benzyl cyanide (1.5 ml, 12.7 mmol) in THF (40 ml) containing HMPA (11 ml, 63.4 mmol) was cooled to −78° C. and treated with lithium bis trimethylsilyamide (16 ml, 16 mmol of 1.0M in THF) dropwise to maintain temperature below −73° C. The reaction was stirred at −78° C. for 1.5 hours. A solution of the product of Example 4, Step B (2.0 g, 6.34 mmol) in THF (8 ml) was added dropwise while the temperature was maintained below −70° C. The reaction temperature was maintained below −68° C. for 3 hours. The reaction mixture was quenched at this temperature with 1N NaHSO$_4$. After warming to room temperature, the mixture was extracted with EtOAc, the combined organic layers were washed with water, saturated NaHCO$_3$, brine, dried (MgSO$_4$), filtered, then concentrated in vacuo. The residue was chromatographed on silica (ethyl/hexanes (5/95)) to afford 1.5 g (67%) of product.

$^1$H NMR (300 MHz, CDCl$_3$,ppm): 7.40-7.30 (m,3H); 7.30-7.22 (m,4H); 7.10 (d,2H); 4.73 (s,2H); 3.98 (t,1H); 3,23-3.08 (m,2H); 0.94 (s,9H); 0.10 (s,6H).

FAB MS: m/e=294 (loss of t-Bu).

Step D: Preparation 3-(4-bromomethyl)phenyl-2-phenylpropionitrile

The product of Example 4, Step C (1.5 g, 4.27 mmol) was treated with CBr$_4$ (1 eq.) and Ph$_3$P (1 eq) in a 1:1 mixture of acetone and acetonitrile, affording in 575 mg (45%) of the title compound after silica chromatography (ethyl acetate/hexanes (5/95)).

$^1$H NMR (300 MHz, CDCl$_3$, ppm): δ7.48-7.10 (m,9H); 4.50 (s,2H); 4.00 (t,1H); 3.26-3.10 (m,2H);.

FAB MS: m/e=299/301.

EXAMPLE 5

4-tert-Butyldimethylsilyloxy-3,5-dipropylbenzyl alcohol

Step A: Preparation of methyl 3-(2-propen-1-yl)-4-(2-propen-1-yloxy)benzoate A solution of 3.04 g (15.8 mmol) of methyl 4-hydroxy-3-propenylbenzoate (Example 42, Step B) was refluxed with anhydrous potassium carbonate (4.37 g, 2 equiv) and allyl bromide (3.5 mL, 2.5 equiv) in acetone overnight. The mixture was filtered through Celite and the filter cake was washed with more acetone and dichloromethane. After removing the solvents, the resulting oil was distilled under high vacuum to give 3.2 g (87%) of the title compound.

$^1$H NMR (400 MHz, CDCl$_3$, ppm): δ7.87 (dd, 1H), 7.83 (d, 1H), 6.83 (d, 1H), 6.07-5.92 (m, 2H), 5.41 (dd, 1H), 5.27 (dd, 1H), 5.07 (dd, 1H), 5.05 (dd, 1H), 4.58 (d, 2H), 3.83 (s, 3H), 3.4 (d, 2H).

Step B: Preparation of methyl 4-hydroxy-3,5-di(2-propen-1-yl)benzoate

The product of Step A (3.2 g, 13.8 mmol) was refluxed in 1,2-dichlorobenzene for 3 days in the presence of a catalytic amount of BHT (10 mg). Flash column chromatography of the mixture using hexane and then 10% and 20% ethyl acetate in hexane afforded 3.1 g (97%) of the title compound.

$^1$H NMR (200 MHz, CDCl$_3$, ppm): δ7.73 (s, 2H), 6.12-5.92 (m, 2H), 5.63 (s, 1H), 5.21 (dd, 2H), 5.15 (dd, 2H), 3.87 (s, 3H), 3.43 (dd, 4H).

FAB-MS: m/e 232 (M+1).

Step C: Preparation of methyl 4-tert-butyldimethylsilyloxy-3,5-di(2-propen-1-yl)benzoate The product of Step B (3.1 g, 13.36 mmol) was treated with tert-butyldimethylsilyl chloride (2.22 g, 1.1 equiv), triethylamine (3 mL) and DMAP (0.1 equiv) in dichloromethane overnight. The mixture was concentrated and flash chromatographed with 5% and then 10% ethyl acetate in hexane to furnish 4.5 g (97%) of the title compound.

$^1$H NMR (200 MHz, CDCl$_3$, ppm): δ7.72 (s, 2H), 6.02-5.30 (m, 2H), 5.12 (dd, 2H), 5.07 (dd, 2H), 3.86 (s, 3H), 3.38 (dd, 4H, 7 Hz), 1.02 (s, 9H), 0.21 (s, 6H).

Step D: Preparation of methyl 4-tert-butyldimethylsilyloxy-3,5-dipropylbenzoate A solution of 5.0 g (14.45 mmol) of the product of Step C in 250 mL ethanol containing 5% Rh/C (0.25 g) was shaken under a 40 psi pressure of hydrogen. Upon completion of reduction, the mixture was filtered through Celite, the filter cake was washed with methanol and dichloromethane. Removal of solvents afforded 4.55 g (90%) of the title compound.

$^1$HNMR (200 MHz, CDCl$_3$, ppm): δ7.66 (s, 2H), 3.84 (s, 3H), 2.54 (dd, 4H, 7.91 Hz, 7.41 Hz), 1.56 (sextet, 4H), 0.98 (s, 9H), 0.899 (t, 6H), 0.18 (s, 6H).

Step E: Preparation of 4-tert-butyldimethylsilyloxy-3,5-dipropylbenzyl alcohol Lithium aluminum hydride (9 mL of a 1M solution in THF) was added cautiously to a solution of the product of Step D at 0° C., and the reaction mixture was stirred overnight. Ethyl acetate was added to the mixture, cooled to 0° C. and treated with cold 1N HCl. After separating the organic phase, the aqueous phase was extracted with a mixture of ethyl acetate-ether-dichloromethane. The combined organic extracts were dried and concentrated. The concentrated material was purified by flash column chromatography using 20% ethyl acetate in hexane to afford 4.2 g (92%) of the title compound.

$^1$H NMR (400 MHz, CDCl$_3$, ppm): δ6.95 (s, 2H), 4.54 (s, 2H), 2.52 (dd, 4H), 1.55 (sextet, 4H), 0.99 (s, 9H), 0.90 (t, 6H), 0.16 (s, 6H).

What is claimed is:

1. A compound of structural formula I

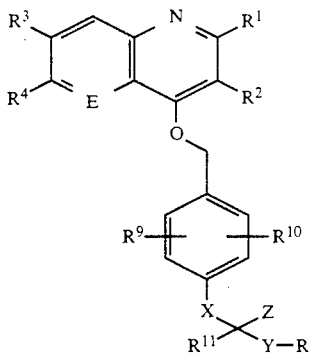

or a pharmaceutically acceptable salt thereof, wherein:
$R^1$ is:
  (a) H,
  (b) $(C_1-C_8)$-alkyl, or
  (c) $(C_1-C_8)$-perfluoroalkyl;
$R^2$ is:
  (a) H,
  (b) $(C_1-C_8)$-alkyl,
  (c) $(C_3-C_8)$-cycloalkyl,
  (d) $(C_3-C_8)$-cycloalkyl-$(C_1-C_4)$-alkyl,
  (e) $CO_2R^{5a}$,
  (f) CN,
  (g) $NO_2$,
  (h) phenyl, or
  (i) phenyl-$(C_1-C_4)$-alkyl;
$R^3$ and $R^4$ are independently:
  (a) H,
  (b) $(C_1-C_6)$-alkyl, unsubstituted or substituted with a substituent selected from the group consisting of:
    (i) $(C_3-C_7)$-cycloalkyl,
  (c) $(C_1-C_6)$-alkoxy,
  (d) $(C_1-C_4)$-perfluoroalkoxy,
  (e) $CF_3$, or
  (f) $(C_1-C_4)$-alkoxycarbonyl;
x is 0 to 2;
E is: CH;
$R^5$ is:
  (a) H, or
  (b) $(C_1-C_6)$-alkyl;
$R^{5a}$ is:
  (a) $R^5$,
  (b) $CH_2$-aryl, wherein aryl is defined as phenyl or naphthyl, or
  (c) aryl, wherein aryl is as defined in $R^{5a}(b)$;
$R^9$ and $R^{10}$ are independently:
  (a) H,
  (b) $(C_1-C_6)$-alkyl, unsubstituted or substituted with $(C_3-C_7)$-cycloalkyl,
  (c) $(C_2-C_6)$-alkenyl,
  (d) $(C_2-C_6)$-alkynyl,
  (e) $(C_1-C_6)$-alkoxy,
  (f) $(C_1-C_6)$-perfluoroalkyl,
  (g) $(C_3-C_7)$-cycloalkyl, unsubstituted or substituted with $(C_1-C_6)$-alkyl,
  (h) $(C_1-C_6)$-alkyl-$S(O)_x$-$(CH_2)_n$-,
  (i) hydroxy-$(C_1-C_6)$-alkyl;
X is:
  (a) —O—,
  (b) —S(O)$_x$—,
  (c) —NR$^{13}$—,
  (e) —OCH$_2$—,
  (f) —NR$^{13}$CH$_2$—,
  (g) —S(O)$_x$CH$_2$—,
  (h) —CH$_2$—,
  (i) —(CH$_2$)$_2$—,
  (j) single bond, or
  (k) —CH=, wherein Y and $R^{12}$ are absent forming a —C=C— bridge to the carbon bearing Z and $R^{11}$;
Y is:
  (a) single bond,
  (b) —O—,
  (c) —S(O)$_x$—,
  (d) —NR$^{13}$—, or
  (e) —CH$_2$—;
except that X and Y are not defined in such a way that the carbon atom to which Z is attached also simultaneously is bonded to two heteroatoms (O, N, S, SO, SO$_2$);
$R^{11}$ and $R^{12}$ are independently:
  (a) H,
  (b) $(C_1-C_6)$-alkyl, unsubstituted or substituted with a substituent selected from the group consisting of:
    (i) aryl, wherein aryl is as defined in $R^{5a}(b)$,
    (ii) $(C_3-C_7)$-cycloalkyl,
  (c) aryl or aryl-$(C_1-C_2)$-alkyl, wherein aryl is as defined in $R^{5a}(b)$ and is unsubstituted or substituted with 1 to 3 substitutents selected from the group consisting of:
    (i) Cl, Br, I, F,
    (ii) $(C_1-C_6)$-alkyl,
    (iii) $((C_1-C_5)$-alkenyl)$CH_2$-,
    (iv) $((C_1-C_5)$-alkynyl)$CH_2$-,
    (v) $(C_1-C_6)$-alkyl-$S(O)_n$-$(CH_2)_n$-,
    (vi) —$CF_3$,
    (vii) —$CO_2R^{5a}$,
    (viii) —OH,
    (ix) —$OCH_3$;
  and can additionally be substituted with 1 or 2 substituents selected from the group consisting of: Br, Cl or F, or
  (d) $(C_3-C_7)$-cycloalkyl;
$R^{13}$ is:
  (a) H,
  (b) $(C_1-C_6)$-alkyl,
  (c) aryl, wherein aryl is as defined in $R^{5a}(b)$,
  (e) $(C_1-C_6)$-alkyl-(C=O)-,
  (f) $((C_2-C_5)$-alkenyl)$CH_2$,
  (g) aryl-$CH_2$-, wherein aryl is as defined in $R^{5a}(b)$;
Z is:
  (a) —$CO_2H$,
  (b) —$CO_2R^{24}$,
  (c) —tetrazol-5-yl, or
  (d) —CONH(tetrazol-5-yl); and
$R^{24}$ is: $(C_1-C_4)$-alkyl.

2. A compound of structural formula:

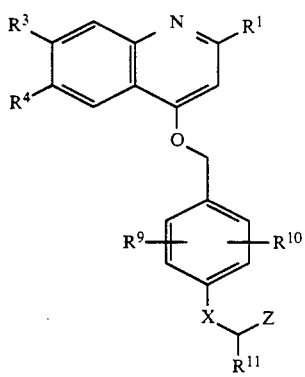

or a pharmaceutically acceptable salt thereof, wherein:
$R^1$ is: $(C_1-C_6)$-alkyl;
$R^3$ and $R^4$ are independently: hydrogen, $(C_1-C_6)$-alkyl or $(C_1-C_6)$-alkoxy;
$R^5$ is: H, $(C_1-C_6)$-alkyl;
$R^9$ and $R^{10}$ are independently:
  (a) H,
  (b) $(C_1-C_6)$-alkyl, unsubstituted or substituted with $(C_3-C_7)$-cycloalkyl,
  (c) $(C_2-C_6)$-alkenyl,
  (d) $(C_2-C_6)$-alkynyl,
  (e) $(C_1-C_6)$-alkoxy, or
  (f) $(C_1-C_6)$-perfluoroalkyl;
X is: O, NH or $CH_2$;
$R^{11}$ is:
  aryl, wherein aryl is defined as phenyl or naphthyl, unsubstituted or substituted with 1 to 3 substituents selected from the group consisting of:
    (i) Cl, Br, I, F,
    (ii) —$CF_3$,
    (iii) —$CO_2R^5$,
    (iv) —$OCH_3$; and
Z is: —$CO_2H$ or —$CO_2$-$(C_1-C_4)$-alkyl.

3. The compound of claim 2 of structural formula:

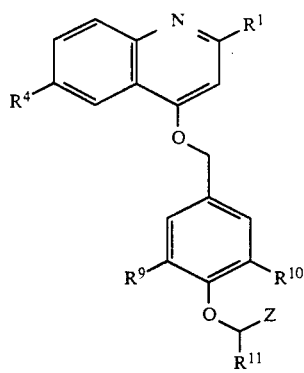

or a pharmaceutically acceptable salt thereof.

4. A pharmaceutical composition useful in the treatment of hypertension which comprises a pharmaceutically acceptable carrier and a therapeutically effective amount of a compound of claim 2.

5. A method of treating hypertension which comprises administering to a patient in need of such treatment a therapeutically effective amount of a compound of claim 2.

6. An ophthalmological formulation for the treatment of ocular hypertension comprising an ophthalmologically acceptable carrier and an effective ocular antihypertensive amount of a compound of claim 2.

7. A method of treating ocular hypertension comprising topical ocular administration to a patient in need of such treatment of an effective ocular antihypertensive amount of a compound of claim 2.

8. A method of treating cognitive dysfunction, anxiety, or depression comprising administering to a patient in need of such treatment, a therapeutically effective amount of a compound of claim 2.

* * * * *